United States Patent [19]

Bach

[11] 4,098,790

[45] Jul. 4, 1978

[54] ERGOLINE CHLORINATION PROCESS

[75] Inventor: Nicholas J. Bach, Indianapolis, Ind.

[73] Assignee: Eli Lilly and Company, Indianapolis, Ind.

[21] Appl. No.: 723,378

[22] Filed: Sep. 15, 1976

[51] Int. Cl.² .................. C07D 457/02; C07D 457/04
[52] U.S. Cl. .................................. 260/285.5; 424/261
[58] Field of Search ...................... 260/285.5; 424/261

[56] References Cited

U.S. PATENT DOCUMENTS

| | | | |
|---|---|---|---|
| 3,732,231 | 5/1973 | Semonsky et al. | 424/261 |
| 3,904,757 | 9/1975 | Slater | 424/261 |
| 3,920,664 | 11/1975 | Clemens et al. | 260/285.5 |
| 3,968,111 | 7/1976 | Bach et al. | 260/285.5 |

OTHER PUBLICATIONS

T. G. Chem. Co.; Chem. Abs. vol. 59: 6538f (1963), Abstract of Japanese patent 3596 (1963).
Bartlett et al.; Chem. Abs. vol. 70: 67683p (1969).

*Primary Examiner*—Richard J. Gallagher
*Assistant Examiner*—Mary Vaughn
*Attorney, Agent, or Firm*—James L. Rowe; Everet F. Smith

[57] ABSTRACT

Ergolines are chlorinated with $SO_2Cl_2/BF_3$·etherate, preferentially in the 2 position.

4 Claims, No Drawings

ERGOLINE CHLORINATION PROCESS

BACKGROUND OF THE INVENTION

Compounds based on the ergoline ring system:

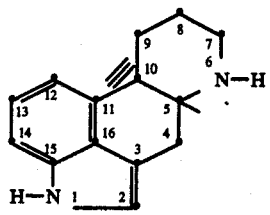

have a suprising variety of pharmaceutical activities. For example, lysergic and isolysergic acid are D-8-carboxy-6-methyl-Δ⁹-ergolines (9,10-didehydroergolines or 9-ergolenes.) The amides of lysergic acid have valuable and unique pharmacologic properties, and include the naturally-occurring peptide alkaloids; ergocornine, ergokryptine, ergonovine, ergocristine, ergosine, ergotamine, etc.; synthetic oxytocic alkaloids such as methergine; and the synthetic hallucinogen - lysergic acid diethylamide or LSD. Ergotamine, a 9-ergolene, with a "peptide" side chain, has been used in the treatment of migraine and recently, both ergocornine and 2-bromo-α-ergokryptine have been shown to be inhibitors of prolactin and of dimethylbenzanthracene (DMBA)-induced tumors in rats, according to Nagasawa and Meites, *Proc. Soc. Exp'tl. Bio. Med.* 135, 469 (1970) and to Heuson et al., *Europ. J. Cancer*, 353 (1970). (See also U.S. Pat. Nos. 3,752,888 L and 3,752,814).

Non-peptide ergot derivatives, both naturally occurring and totally or partially synthetic, share these multiple pharmacological properties with the peptide derivatives. For example, D-6-methyl-8-cyanomethylergoline, was prepared by Semonsky and co-workers, *Coll. Czech. Chem. Commun.*, 33, 577 (1968), and was found to be useful in preventing pregnancy in rats - *Nature*, 221, 666 (1969). (See also U.S. Pat. No. 3,732,231) - by interfering with the secretion of hypophysial leuteotropic hormone and the hypophysial gonadotropins or by inhibiting the secretion of prolactin. [See Seda et al., *Reprod. Fert.*, 24, 263 (1971) and Mantle and Finn, id. 441)]. Semonsky and co-workers, *Coll. Czech. Chem. Comm.*, 36, 220 (1971), have also prepared D-6-methyl-8-ergolinylacetamide, a compound which is stated to have anti-fertility and anti-lactating effects in rats. The 2-halo derivatives of D-6-methyl-8-cyanomethylergoline and of D-6-methyl-8-ergolinylacetamide have been prepared and found to be active prolactin inhibitors (M. J. Sweeney, J. A. Clemens, E. C. Kornfeld and G. A. Poore, 64th Annual Meeting Amer. Assoc. Cancer Research, April, 1973 - See also U.S. Pat. No. 3,920,664).

D-2-chloro-6-methyl-8-cyanomethylergoline (generic name, lergotrile), one of the aforementioned 2-halo derivatives, can be prepared by chlorinating D-6-methyl-8-cyanomethylergoline with such halogenating agents as N-chlorosuccinimide, N-chloroacetanilide, N-chlorophthalimide, N-chlorotetrachlorophthalimide, 1-chlorobenzotriazole, N-chloro-2,6-dichloro-4-nitroacetanilide, N-chloro-2,4,6-trichloroacetanilide, and sulfuryl chloride. Lergotrile can also be prepared by chlorinating any of the intermediate compounds used by Semonsky et al. (loc. cit.) for the preparation of D-6-methyl-8-cyanomethylergoline including methyl dihydrolysergate or D-6-methyl-8-hydroxymethylergoline, or with the novel intermediate of Example 6 of U.S. Pat. No. 3,920,664 such as, D-6-methyl-8-methylsulfonyoxylmethylergoline.

It is an object of this invention to provide a method of chlorinating any of the above ergoline derivatives to provide either lergotrile or a compound readily convertible thereto in higher yield than with any of the chlorinating agents heretofor provided by the art.

SUMMARY OF THE INVENTION

In fulfillment and other objects, this invention provides a process for chlorinating in the 2-position an ergoline of the following structure:

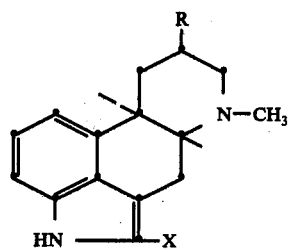

wherein R is carbo-$C_1$—$C_3$-alkoxy, ($C_1$—$C_4$-alkoxycarbonyloxy)methyl, hydroxymethyl, halomethyl, ($C_1$—$C_4$-alkylsulfonyloxy)methyl, or cyanomethyl and X is H, to prepare a compound wherein R is as defined and X is Cl.

The above chlorination step is carried out by suspending or dissolving an ergoline according to Formula I wherein X is H in an inert solvent, as for example acetonitrile, nitromethane, methylene dichloride, etc. Ordinarily the suspension or solution is cooled to a temperature in the range −10° to 10° C. An excess (2—3 fold) of boron trifluoride etherate is then added, upon which addition the suspended ergoline, if not already in solution, dissolves. An excess (10 percent usually) of sulfuryl chloride in an inert solvent such as methylene dichloride is next added in dropwise fashion. The reaction mixture is stirred under cooling for about 15 minutes and the reaction is then quenched by dilution with an aqueous base such as 10 percent aqueous ammonium hydroxide. The 2-chloroergoline thus produced is then extracted into a water-immiscible organic solvent and the organic layer separated. The separated organic solution is then washed with, for example, a saturated aqueous sodium chloride solution or otherwise purified, separated again, and then dried. Evaporation of the solvent yields, as a residue, a 2-chloroegoline according to Formula I above (wherein X is chloro) formed in the above reaction. The 2-chloroergoline can be further purified by chromatography or crystallization. Yields of the chlorinated compound vary from 40 to 75 percent with a majority of runs giving in excess of 70 percent of the desired compound.

The use of boron trifluoride etherate as an adjunct in the conventional sulfuryl chloride chlorination not only increases the yield of chlorinated product by solubilizing the ergoline to yield a homogenous rather than a heterogenous reaction system, but also apparently directs the chlorination preferentially to the 2-position of the ergoline ring, thus lessening the quantity of by-product formed and increasing the yield of the desired 2-chloroderivative.

While the process of this invention is useful when applied to compounds according to Formula I where X is H and R is as defined, it is particularly valuable in terms of overall chlorination yields, ease of handling on a plant scale, etc. when applied to starting materials according to Formula I wherein X is H and R is —CO—O—$C_1$—$C_3$-alkyl, —$CH_2$—O—CO—O—$C_1$—$C_3$-alkyl or —$CH_2$—O—$SO_2$—$C_1$—$C_4$-alkyl.

In Formula I above, when R is carbo-$C_1$—$C_3$-alkoxy (CO—O—$C_1$—$C_3$-alkyl), the term includes such groups as carbomethoxy, carboethoxy or carbopropoxy, the compounds in question being the methyl, ethyl, n-propyl and isopropyl esters of dihydrolysergic acid. When R is halomethyl, the term includes chloromethyl, bromomethyl and iodomethyl. When R is ($C_1$-$C_4$ alkoxycarbonyloxy)methyl, the term includes the formyl, acetyl, propionyl and butyryl carbonates of D-6-methyl-8-hydroxymethylergoline or of its 2-chloro derivative. When R is ($C_1$-$C_4$ alkylsulfonyloxy)methyl, the term includes the methylsulfonyl (mesyl), n-propylsulfonyl, isobutylsulfonyl and the like esters of the 8-hydroxy methyl compound.

As previously stated, the process of this invention is useful in preparing the active prolactin inhibitor and anti-Parkinson drug, lergotrile (Formula I when R is —$CH_2$—CN and X is Cl) when a compound according to Formula I when X is H and R is —$CH_2$—CN is chlorinated. The process is also useful in synthesizing intermediates which can be converted to lergotrile. For example, chlorination of an ester of dihydrolysergic acid yields an ester of 2-chlorodihydrolysergic acid. Reduction of the ester group with $LiAlH_4$ yields D-2-chloro-6-methyl-8-hydroxymethylergoline. This compound can then be converted to a 2-chloro-8-halomethyl derivative or can be esterified to yield, for example, the 2-chloro-8-mesyloxymethyl derivatve. Either of these derivatives can be readily converted to the 2-chloro-8-cyanomethyl compound (lergotrile). In addition, any of the above intermediates, the 8-hydroxymethyl compound, the 8-halomethyl compounds or the esters of the 8-hydroxymethyl compound can also be prepared by direct chlorination in the 2-position of the corresponding unchlorinated derivative by the process of this invention. As before, these 2-chlorointermediates can be converted to lergotrile by the processes set forth in the prior art.

This invention is further illustrated by the following specific examples.

EXAMPLE I

Chlorination of D-6-methyl-8-cyanomethylergoline 810 mg. of D-6-methyl-8-cyanomethylergoline were suspended in 50 ml. acetonitrile and the suspension cooled to —5° to 0° C. 1.25 ml. of boron trifluoride etherate were added thus solubilizing the ergoline. Next, a solution of 0.27 ml. of sulfuryl chloride in 20 ml. of methylene dichloride was added in dropwise fashion. The reaction mixture was stirred and cooled for 30 minutes, then diluted with ammonium hydroxide. The diluted solution was extracted with a chloroform-isopropanol 3:1 solvent mixture. The organic layer was separated, washed with a saturated aqueous sodium chloride solution, dried and the solvent evaporated. The residue comprising lergotrile formed in the above chlorination procedure was chromatographed over fluorosil using chloroform containing 2 percent methanol as the eluant; 660 mg. of lergotrile were obtained melting at 268°-271° C. (with decomposition), 72 percent yield.

The above reaction was repeated but using nitromethane in place of acetonitrile as a solvent for the ergoline. The yield was 66 percent.

EXAMPLE 2

Chlorination of D-6-methyl-8-hydroxymethylergoline 770 mg. of D-6-methyl-8-hydroxymethylergoline were suspended in 50 ml. of acetonitrile. The suspension was cooled to a temperature in the range —5° to 0° C. About 1.25 ml. of boron trifluoride etherate were added, and the suspended ergoline dissolved. Next, 0.27 ml. of sulfuryl chloride dissolved in 20 ml. of methylene dichloride were added in dropwise fashion. The reaction mixture was stirred under cooling for about 15 minutes and then diluted with dilute aqueous ammonium hydroxide. D-2-chloro-6-methyl-8-hydroxymethylergoline formed in the above reaction was isolated and purified by the procedure of Example 1. The residue was chromatographed over 30 g. of fluorisil using chloroform containing 5 percent methanol as the eluant. 340 mg. of D-2-chloro-6-methyl-8-hydroxymethylergoline melting at 259°-261° C. (with decomposition) were obtained; yield = 40%.

EXAMPLE 3

Chlorination of D-6-methyl-8-mesyloxymethylergoline 855 mg. of D-6-methyl-8-mesyloxymethylergoline were suspended in 50 ml. of nitromethane. The suspension was cooled to a temperature in the range —5° to 0° C. About 1.25 ml. of boron trifluoride etherate were added resulting in immediate solution of the ergoline. A solution of 0.23 ml. of sulfuryl chloride in 20 ml. of methylene dichloride was next added in dropwise fashion. The reaction mixture was stirred under cooling for 30 minutes and then the 2-chloroergoline isolated and purified by the procedure of Example 1. Chromatography over 30 g. of fluorosil using chloroform containing 2 percent methanol as the eluant yielded 610 mg. (65 percent yield) of D-2-chloro-6-methyl-8-mesyloxymethylergoline melting at 140°-3° C.

Other alkylsulfonylesters of D-6-methyl-8-hydroxymethylergoline can be chlorinated in similar fashion.

EXAMPLE 4

Chlorination of Methyl Dihydrolysergate 885 mg. of methyl dihydrolysergate were dissolved in 50 ml. of methylene dichloride. 0.95 ml. of boron trifluoride etherate were added and the reaction mixture cooled to a temperature in the range 0°-5° C. A solution of 0.27 ml. sulfuryl chloride in 20 ml. of methylene dichloride was added in dropwise fashion. The reaction mixture was stirred and cooled for about 15 minutes and then quenched by pouring into an ice-dilute ammonium hydroxide mixture. D-2-chloro-6-methyl-8-carboxyergoline, methyl ester or methyl 2-chlorodihydrolysergate formed in the above reaction was isolated and purified by the procedure of Example 1. Chromatography over fluorosil using 2 percent methanol in chloroform yielded 730 mg. (74 percent yield) of crystalline material melting at 206°-8° C. with decomposition.

Other esters of dihydrolysergic acid such as the ethyl, the n-propyl, and the isopropyl esters can be chlorinated to yield the corresponding 2-chloro compound by the above procedure.

EXAMPLE 5

Chlorination of D-6-Methyl-8-methoxycarbonyloxymethylergoline 960 mg. of D-6-methyl-8-methoxycarbonyloxymethylergoline were suspended in 50 ml. of acetonitrile and the suspension cooled to a temperature in the range 0°–5° C. 1.25 ml. of boron trifluoride etherate were added followed by the dropwise addition of 0.27 ml. of sulfuryl chloride in 25 ml. of methylene dichloride. The reaction mixture was stirred with cooling for about 30 minutes and D-2-chloro-2-methyl-8-methoxycarbonyloxymethylergoline formed in the above reaction was isolated by the procedure of Example 1. Chromatography using chloroform containing 1 percent methanol as the eluant yielded 785 mg. (74 percent yield) of D-2-chloro-6-methyl-8-methoxycarbonyloxymethylergoline melting at 161°–3° C.

The above procedure can equally well be applied to the chlorination in the 2 position of D-6 -methyl-8-ethoxycarbonyloxymethyl ergoline and to the chlorination of corresponding n-propyl and isopropyl carbonate esters of D-6-methyl-8-hydroxymethylergoline.

The procedure of Example 1 can also be applied to the chlorination of the D-6-methyl-8-halomethylergolines to yield D-2-chloro-6-methyl-8-chloromethylergoline, D-2-chloro-6-methyl-8-bromomethylergoline, and D-2-chloro-6-methyl-8-iodomethylergoline.

Starting materials useful in the process of this invention (those compounds according to Formula I wherein X is H) are readily available. Methyl dihydrolysergate is a well-known compound, as are the higher alkyl esters of dihydrolysergic acid. The reduction of the ester group with lithium aluminum hydride to yield compounds in which X is H and R is hydroxymethyl (also known as D-dihydrolysergol) are prepared by the procedure of Semonsky et al. *Coll. Czech. Chem. Commun.*, 33, 577 (1968). The conversion of this intermediate to compounds wherein X is H and R is halomethyl are carried out by the procedure of Semonsky et al. U.S. Pat. No. 3,732,231 as is the preparation of the 8-cyanomethyl derivatives. U.S. Pat. No. 3,920,664 discloses the preparation of the corresponding 8-bromomethyl compounds and the 8-mesyloxymethyl compounds as well as their conversion to 8-cyanomethyl compounds. The lower alkoxycarbonyl esters of the 8-hydroxymethyl compounds useful as starting materials in Example 5 above are prepared in analogous fashion to the mesyloxy esters.

Starting material according to Formula I wherein X is H and R is $C_1$–$C_4$ alkyl sulfonyloxymethyl are prepared by the procedure of Example 6 of U.S. Pat. No. 3,920,664 which discloses specifically the preparation of the D-6-methyl-8-mesyloxymethylergoline. The corresponding n-butylsulfonyloxy derivative (D-6-methyl-8-n-butylsulfonyloxymethylergoline) is prepared by the reaction of n-butylsulfonyl chloride on hydroxymethylergoline in the presence of pyridine. This ester has the unexpected property of being soluble in the inert solvents employed in the chlorination process of this invention unlike the mesyl ester of D-dihydrolysergol. D-6-methyl-8-n-butylsulfonylmethylergoline melts at 168°–9° C. after recrystallization from methanol.

Analysis; Calculated: C, 63,80, H; 7.50; N; 7.44; S; 8.52; Found: C, 63.62; H; 7.40; N; 7.19; S; 8.41.

I claim:

1. The process which consists essentially of the step of chlorinating an ergoline of the formula:

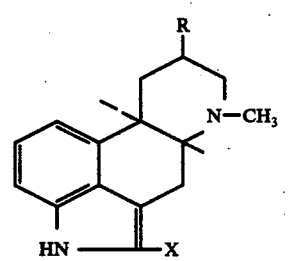

wherein R is carbo-$C_1$—$C_3$ alkoxy, ($C_1$—$C_4$-alkoxycarbonyloxy) methyl, hydroxymethyl, halomethyl, ($C_1$—$C_4$ -alkylsulfonyloxy) methyl or cyanomethyl and X is H with sulfuryl-chloride in the presence of boron trifluoride etherate in an inert solvent to yield a compound of the above formula wherein R is as defined and X is Cl.

2. A process according to claim 1 wherein the sulfurylchloride and boron trifluoride etherate are present in a molar excess based upon the number of moles of ergoline present.

3. D-6-methyl-8-n-butylsulfonyloxymethylergoline.

4. The process which consists essentially of the step of chlorinating an ergoline of the formula:

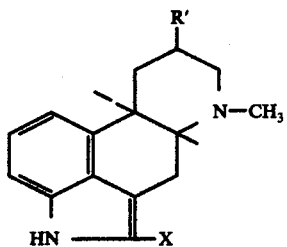

wherein R' is —CO—O—$C_1$—$C_3$-alkyl, —CH$_2$—O—CO—O—$C_1$—$C_3$-alkyl or —CH$_2$—O—SO$_2$—$C_1$—$C_4$ alkyl and X is H with sulfurylchoride in the presence of BF$_3$. etherate in an inert solvent to yield a compound of the above formula wherein R' is as defined and X is Cl.

* * * * *